(12) United States Patent
Kurple

(10) Patent No.: US 8,924,239 B1
(45) Date of Patent: Dec. 30, 2014

(54) METHOD AND APPARATUS FOR MONITORING CALORIE, NUTRIENT, AND EXPENSE OF FOOD CONSUMPTION AND EFFECT ON LONG TERM HEALTH AND SHORT TERM STATE

(71) Applicant: Maureen Kurple, Fairlawn, OH (US)

(72) Inventor: Karl Vincent Kurple, Fairlawn, OH (US)

(73) Assignee: Maureen Kay Kurple, Fairlawn, OH (US)

( * ) Notice: Subject to any disclaimer, the term of this patent is extended or adjusted under 35 U.S.C. 154(b) by 0 days.

(21) Appl. No.: 14/051,770

(22) Filed: Oct. 11, 2013

Related U.S. Application Data

(63) Continuation-in-part of application No. 13/367,335, filed on Feb. 6, 2012, now abandoned, which is a continuation of application No. 12/249,898, filed on Oct. 10, 2008, now abandoned.

(60) Provisional application No. 60/978,759, filed on Oct. 10, 2007.

(51) Int. Cl.
*G06Q 50/00* (2012.01)
*G06F 19/00* (2011.01)

(52) U.S. Cl.
CPC .................. *G06F 19/3475* (2013.01)
USPC .................................................. 705/3; 705/2

(58) Field of Classification Search
CPC . G06F 19/3475; G06F 19/3431; G06Q 50/22; G06Q 50/24
USPC ......................................................... 705/2–3
See application file for complete search history.

(56) References Cited

U.S. PATENT DOCUMENTS

| | | | |
|---|---|---|---|
| 6,980,999 B1 * | 12/2005 | Grana | 707/803 |
| 2002/0027164 A1 * | 3/2002 | Mault et al. | 235/462.46 |
| 2005/0113650 A1 * | 5/2005 | Pacione et al. | 600/300 |
| 2009/0099873 A1 * | 4/2009 | Kurple | 705/3 |

* cited by examiner

*Primary Examiner* — Sind Phongsvirajati
(74) *Attorney, Agent, or Firm* — Stephen D. Schrantz; Schrantz Law Firm, PLLC

(57) ABSTRACT

A system for improving health and monitoring diet has been developed which enables a consumer before making important decisions which effect health to consider health, nutrition, dietary, budget, and time information resources more easily before decisions are made. The system has a variety of user inputs that enable the user to access information easily and enter information easily, so that the personal profile and health history and diet information is up-to-date. This system is adjustable to contain additional modules of information such as dietary restrictions which can be used to regularly recommend or restrict purchase decisions at the point of sale, storage, preparation, or consumption.

20 Claims, 8 Drawing Sheets

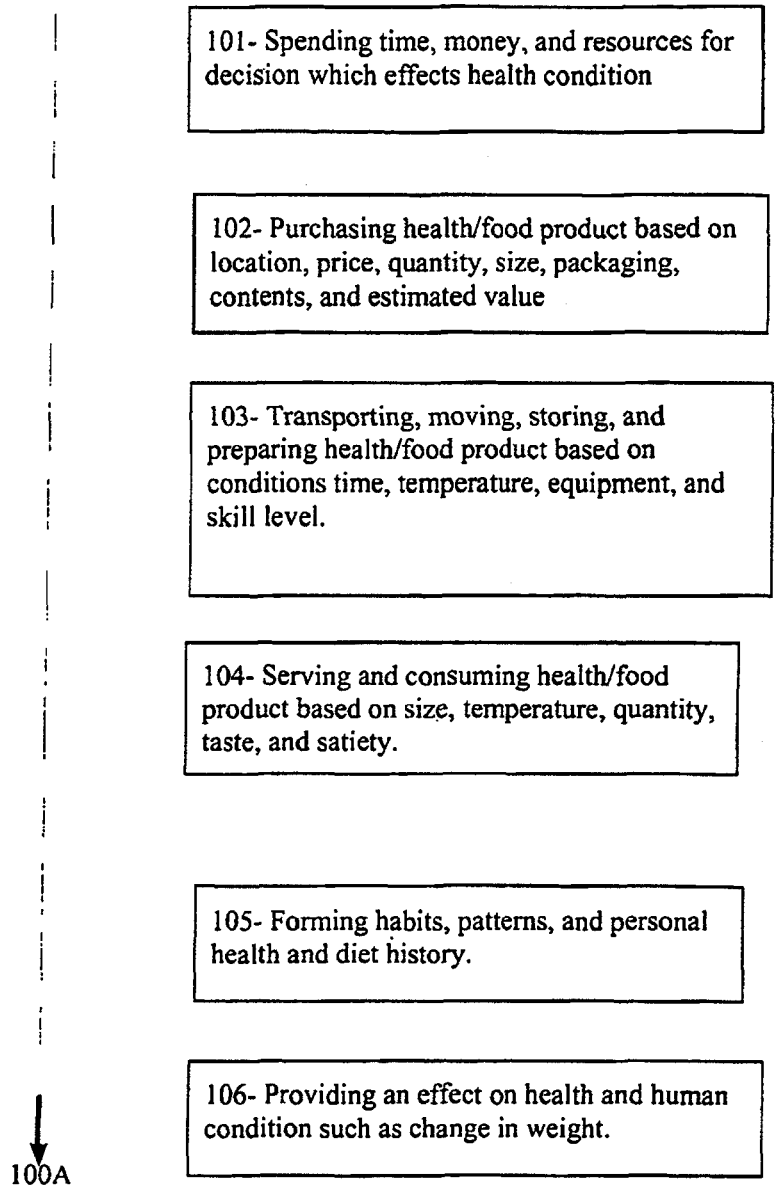

200A

| ** Suggested Next | Meals | | |
|---|---|---|---|
| 10/8/2007 | | **Meal #4545 | Weekly Meal high in K, Zn suggested |
| 10/8/2007 | | **Meal #4321 | Weekly Meal high in K, V suggested |

METHOD AND APPARATUS FOR MONITORING CALORIE, NUTRIENT, AND EXPENSE OF FOOD CONSUMPTION AND EFFECT ON LONG TERM HEALTH AND SHORT TERM STATE

CROSS-REFERENCE TO RELATED APPLICATIONS

This application claims priority to and is a continuation-in-part of U.S. patent application Ser. No. 13/367,335 filed on Feb. 6, 2012 entitled METHOD AND APPARATUS FOR MONITORING CALORIE, NUTRIENT, AND EXPENSE OF FOOD CONSUMPTION AND EFFECT ON LONG TERM HEALTH AND SHORT TERM STATE, which is a continuation of U.S. patent application Ser. No. 12/249,898 filed on Oct. 10, 2008 entitled METHOD AND APPARATUS FOR MONITORING CALORIE, NUTRIENT, AND EXPENSE OF FOOD CONSUMPTION AND EFFECT ON LONG TERM HEALTH AND SHORT TERM STATE, which is a continuation in part of U.S. Patent Application No. 60/978,759 filed on Oct. 10, 2007 which are hereby incorporated by reference.

STATEMENT REGARDING FEDERALLY SPONSORED RESEARCH OR DEVELOPMENT

Not Applicable.

REFERENCE TO A MICROFICHE APPENDIX

Not Applicable.

RESERVATION OF RIGHTS

A portion of the disclosure of this patent document contains material which is subject to intellectual property rights such as but not limited to copyright, trademark, and/or trade dress protection. The owner has no objection to the facsimile reproduction by anyone of the patent document or the patent disclosure as it appears in the Patent and Trademark Office patent files or records but otherwise reserves all rights whatsoever.

FIELD OF THE INVENTION

This invention is in the field of food intake monitoring and health improvement.

BACKGROUND OF THE INVENTION

US Pat. Pub. 20040039661 (hereby incorporated by reference), US Pat. Pub. 20020079367 (hereby incorporated by reference), U.S. Pat. No. 6,246,998 (hereby incorporated by reference), U.S. Pat. No. 5,794,207 (hereby incorporated by reference), U.S. Pat. No. 5,832,497 ((hereby incorporated by reference), U.S. Pat. No. 5,842,185 (hereby incorporated by reference), U.S. Pat. No. 6,356,940 (hereby incorporated by reference), U.S. Pat. No. 6,980,999 (hereby incorporated by reference), U.S. Pat. No. 6,496,809 (hereby incorporated by reference), U.S. Pat. No. 6,527,712 (hereby incorporated by reference), and U.S. Pat. No. 6,978,221 (hereby incorporated by reference) disclose various systems for making decisions, recording information, and managing transactions.

There are several known methods of monitoring health based upon food intake or diet. With these methods, the amount of calories is attempted to be reduced over time. Typically, attempting to lower the consumption of calories is thought to lower weight. Some diets pay attention to food, food types, and food groups consumed, and the benefit certain food groups and their contents have over other food groups. An additional concern for some diets is the amount of certain food groups such as protein, carbohydrate, or fats in relation to each other. For example, often fats are seen as less desirable because they contain more energy and may have twice as many calories as carbohydrates. In addition, it is also desirable to maintain the weight loss over extended periods of time.

In the field of dieting, there are several methods that attempt to optimize the amount of weight loss without compromising the long term health, energy level, or mood. Most diet programs are directed towards weight reduction which is accomplished by seeking to reduce the amount of calories the dieter consumes. Also, many diets seek to reduce the amount of calories without changing the amount of food the dieter eats. However, these diets may require special foods that incur additional expense, time, and change to the dieters routine. One of the most effective routines for changing a person's behavior is making them record their decisions and write down their options before making their next decision. Still, many dieters struggle with compliance and as a result their ability to stay on a diet and report information accurately is frequently proportional. Food has important benefits, but because it is difficult to track systematically effect of many important foods, more powerful medicines are used instead.

None of the methods in the prior art employ a systematic approach to determine a dieter's goals based on an accurate measurement of the food they are currently consuming and changing the amount of foods they are actually purchasing for consumption. None of the previous methods take advantage of tracking a person's consumption and eating habits can provide a vital perspective to a person's nutritional health and diet decisions. By changing the decisions they make to purchase and consume food before the food is purchased or consumed. Additionally, this health improvement and diet monitor system is able to accurately measure the foods actually consumed and provide better diet management based on this accurate and easily accessible information.

SUMMARY OF THE INVENTION

A method has been devised for high volume, highly accurate measurement and monitoring of food consumption and corresponding nutritional information. The food purchases and food consumed are easily monitored and stored in electronically readable format that can be easily accessed and analyzed for making health decisions. The structure which carries out the method is also disclosed herein. The structure which carries out this method is a computer system which is directed by a computer program to exchange information between multiple databases and receive information from several different user interfaces. In this system, the nutritional information for a food purchase must be retrieved for each individual purchase after purchase or consumption has occurred. These systems typically do not have means of recording the information and presenting the information that can affect and plan future food purchase and consumption decisions. Normally, diet plans are sold to consumers along with special foods. Compliance on the part of the consumer on the diet is not carefully measured, the longer the person attempts to stay on the diet by purchasing special foods or paying program fees, the diet continues and the program makes money. The actual effect on health may not be monitored as often as the desired weight reduction. Often weight reduction is suggested to help manage other health problems ranging from diabetes, hypertension, and back pain. Weight reduction is typically primarily monitored early on in the diet by calorie consumption. This in turn yields relatively little information about the effect of improving health or changing habits or providing other important benefits to the consumer such as increased energy, increased physical and mental functioning, increased lifespan, or reduced time and money spent on food and eating and trips to the doctor or grocery store. Weight change can also be used to monitor progress. However, this is also not a direct measure of the consumer's compliance on the diet.

In some cases, compliant dieters may reduce calories or achieve other dietary restrictive goal, but fail to lose weight. In other cases, short term weight reduction may occur, but long term health benefits or consistent weight reduction is not maintained. In most cases, the reason the dieter fails to achieve the desired goal long term is unclear, due to a lack of both long term compliance as well as enough long term basic information on diet and eating habits.

The method described herein utilizes steady monitoring of diet which generates not only information about the health and diet during periods of attempted dieting, but also monitors the diet and other health measurements when no special dieting is being attempted. Optionally, as disclosed hereinbelow a computer system may be used to monitor the process and provide valuable feedback before additional food consumption and purchases are made on a daily or meal-to-meal basis if desired.

Weight increases or decreases as a function of calorie consumption do not provide a correlation that provides enough information in a timely or precise manner. Further, weight reduction does not indicate the complete picture of the most relevant health issues a person may be facing. By utilizing a fuller set of data gathering and storage devices to record information on diet and health over the long term a more systematic approach to improving health through diet can be accomplished.

Hence, the disclosed system is potentially simpler than diet programs. Instead of operating under the assumption that changes should be made to the diet before knowing actually what the person's regular diet is. This system can actually record and measure the existing diet and eating habits and develop a program based on goals and suggested input from the consumer and the consumer's medical and health advisors based on actual data of what the consumer is eating on a regular basis. Furthermore, specific changes of the greatest importance can then be introduced and monitored directly. For example, instead of suggesting only weight reduction through calorie restriction, more specific plans targeting particular nutrient level and combinations of foods to provide that nutrient level or ratio can be targeted to improve a specific ailment like hypertension or depression in a more focused way. With this more precise diet monitoring, one would be able to tell if the change in the specific intake of a recommended nutrient is having the desired health effect. As a result, it is possible to know more clearly if the diet is actually changing, and if a changed diet is producing the desired effect on health. Further, this system introduces important information back at the point when diet decisions which effect health are actually made such as meal planning, food purchasing, and food consumption.

Attempting to improve health with diet is not a new technology. There are different techniques utilized which depend on the objective function of the diet. In any diet application, quality is ultimately measured by how well the person achieves the desired effect which is usually weight loss. Regardless if the person managed to follow the diet and fail to achieve the ultimate goal of the proposed diet such as the reduced health risk or improvement in health due to the weight loss. There are also the issues of food preparation, individual allergies, and metabolism that may outweigh the attempt to measure the compliance and success of the diet based on the weight reduction alone. The goal is to achieve a positive change in health that is not limited to only restricting calorie consumption or reducing weight.

Stomach does not have a full sensor and a separate nutrition sensor. Nutritional deficiencies are expressed throughout the body in a lack of energy, lack of health, pain, sickness, or discomfort. It is an object of the invention to avoid waiting for the health problems to occur in the body before correcting the problems or deficiencies in the diet. An apparatus for entering and storing foods consumed or electronic media to form a personal account comprising by a diet history comprised by foods consumed by a particular consumer, a food database containing nutritional information on foods consumed as well as foods purchased and foods available for purchase, a calendar function that records and measures the consumption and purchase of foods over time, and a database program that is capable of comparing or performing analysis on the food values to set values or values in the food database. Another embodiment of the invention includes an apparatus which is comprised by a database of personal health information which can be accessed and updated remotely, database of diet history, general health information guide which includes data value ranges which are indicative of health problems, and a search engine which is able to scan the database of diet history against the general health information guide for signs of illness or nutritional deficiencies.

Furthermore, the effect of a change in the diet should be understood in terms of its effect on the health of the entire person. Because of all the requirements for diet, attention to calorie consumption, monitoring specific food groups, purchase of expensive foods produced by the diet program, and changing many aspects of diet too quickly, it is difficult to achieve the desired health benefits with a typical diet approach. As described briefly above, the instant invention utilizes a systematic approach to accurately and comprehensively measuring all aspects of the diet, so that specific changes can be better understood before changes are made and the compliance of the consumer on the and therefore the benefit of the diet can be determined. The particular diet monitoring approach systematically generates important nutritional information which can be coordinated with both long term dietary and health goals.

Additionally, certain problems like celiac disease can only diagnosed with adequate information about the diet. However, adequate time and attention is not usually placed on the patient's diet history by the physician to lack of record keeping or accurate long term details by the patient. As a result, a valuable non-invasive, low cost source of information and tool for more accurately diagnosing disease, identifying problems with diet, digestion, nutrient absorption, or improving health is lost to the patient. Screening the diet and specifically the nutritional history of an individual provides a non-invasive, low cost way to investigate health. Further, nutritional information is important for treating and preventing disease as adequate nutrition can help strengthen immune system and energy level of the body. Additionally, levels of certain compounds can be effective as markers for risk of disease. In particular, homocysteine levels can be used as a marker for risk factor for cardiovascular disease.

In addition to calorie consumption, there are other factors which may affect digestion and ultimately how many calories and which nutrients are absorbed. Counting calories does not consider those cases of food allergies or food intolerances where a particular may not be able to extract any calories from food despite the calorie value obtained from a bomb calorimeter. In addition, the quality of digestion may make a significant contribution to the amount of calories that are released and the nutrients are assimilated. Simple factors such as temperature of the food may contribute to the quality of the digestion. It has been demonstrated that in cultures where meals are followed by hot tea, nutrient absorption and digestion is improved. The temperature of the food ingested can be approximated in this invention using sensors as well as using approximate serving size and serving temperatures.

Further, the effectiveness of most diets is based on weight reduction which is determined by weight measurement. This is an ineffective way to measure the effectiveness of a diet to provide health to the consumer on the diet or compliance of the consumer on the diet. Weight management does not provide information quickly enough or specific to each day or meal or specific nutrient or food to show the effect of these specific inputs accurately over both very long or very short time intervals.

Further, other variables in addition to those concerning consumption may give false readings as to the effectiveness of the diet. General health, physical activity, stress level, illness, food allergies, food intolerances, and other factors affecting enzyme, hormone, glycemic index, and overall health and eating habits may prevent weight measurement from accurately measuring compliance with a diet and effectiveness of the diet.

In addition, as a result of the emphasis on weight change, the calorie content of foods is over emphasized in proportion to the value of the data it provides. Calorie content is determined primarily based on how much heat is released from food when burned in bomb calorimeter. This value for heat in a closed inanimate system does not provide sufficient information for how certain foods may ultimately release the energy or affect health of humans in real life. For example, according to a diet which monitors calorie consumption 100 calories of bread may be considered the same as 100 calories of steak, but in reality 100 calories of these two different foods contain much different nutrient profile and will they have much different effects on the energy level of the consumer.

Through the use of electronic memory and networking with computers it is possible to record and transmit information that is more accurate, valuable, and convey a better overall picture of human health. Using databases more information can be provided quickly to provide fuller information before a decision and record more information after a decision is made. Further, these databases can be searched with larger key search fields. In particular, more information concerning food and nutrient can be recorded, monitored, and tracked to provide a clearer picture of a consumer's health more quickly and more often than calorie consumption. Additionally, specific modules or diet programs can be loaded and tracked to ensure the specific aspects of the diet program are recorded and monitored. But more importantly, more accurate and precise categories of information can be received from the consumer to monitor the effect and long term improvement on human health. Rather, than track only calorie consumption and record weight gain, more and better sources of information can be monitored that will correlate more closely with energy level and optimum health in real time or with higher frequency feedback to monitor progress or effectiveness of potential changes to health. These factors through the use of database and computer networking and sensors to retrieve information can track specific information for the consumer on a customized person-to-person basis based on their particular goals, needs, budget, test values, genetics, and dietary considerations.

Two factors that are considered to provide much more precise information than calorie counting and weight gain are blood sugar level and metabolic rate. To better measure the effect of diet on energy release and effect on consumer health by tracking blood sugar level. Blood sugar can provide a measurement that can be tracked and monitored daily and correlates more closely with shorter delay with the consumer's health, digestion, diet effectiveness through the consumer's measurable and observable energy level and mood.

There is some correlation between calorie consumption and blood sugar level and between calorie consumption and energy level. However, these relationships are not as direct as the relationship between blood sugar level and energy level. Calorie consumption treats all foods and individuals the same, regardless if certain foods lead to any energy release in certain consumers with digestive problems, allergies, hormone problems, or other problems which in some cases for some people results in far less energy than the calories derived from bomb calorimetry values reaching the consumer. Blood sugar level more accurately the amount of energy that is directly available to a consumer following food consumption. It is specific to each individual and measures directly the amount of energy available to a consumer following consumption of a particular food.

Further, one of the greatest factors that affects how people feel and how much energy they have is determined by hormones. This system would enable the information concerning hormone level to be monitored and tracked to determine an effective correlation to diet. In one sense, monitoring blood sugar levels will provide an effective overall measurement of how effective a number of different hormones are working to release energy to the body following food consumption. Blood sugar levels are an effective and inexpensive path to monitoring a number of other risk factors. Monitoring blood sugar levels is less expensive than tracking a number of other hormones. Further, in addition to diabetes, tracking of and monitoring of blood sugar level may also be a more effective measurement to monitor physical activity as well as to stabilize behavioral or mood disorders.

The body's energy level and eating pattern is largely affected by the use and storage of glucose, a cellular fuel. Glucose and its levels throughout the body are closely regulated. Following ingestion of a meal, glucose and other monomers are absorbed into the blood from the digestive tract. If the level of glucose in the blood rises beyond a set level, the pancreas secretes insulin, a hormone into the blood. Insulin then is able to enhance the transport of glucose into body cells and stimulate the liver and muscle cells to store glucose as glycogen. Following this regulation of glucose levels by the body, the blood glucose level drops. When the glucose level falls below the set level, the pancreas secretes the hormone glucagon, which acts opposite of the effect of insulin. Glucagon promotes the breakdown of glycogen and the release of glucose into the blood, increasing the blood glucose level.

Recent studies suggest additionally that there is a complex feedback mechanism that regulates fat storage and use in humans. An increase in adipose tissue increases leptin, hormone levels in blood. A high level of leptin signals the brain to increase consuming muscular activity and suppress appetite. Loss of body fat decreases leptin levels in the blood, signaling the brain to increase appetite and weight gain.

Although there are numerous feedback mechanisms which have been found to help regulate body weight, blood glucose has one of the most direct relationships on metabolism. Metabolic balance depends on the maintenance of blood glucose at a concentration near a set point, which is about 90 mg/100 mL. When blood glucose levels are higher than this level, insulin is released and acts to lower the blood glucose concentration. When blood glucose levels fall beneath this set value, glucagon is released and acts to lower to increase the glucose concentration. Insulin works to lower blood glucose levels by stimulating all body cells expect those of the brain to take up glucose from the blood. Because brain has access to fuel all the time, it is affected by how much glucose remains in the blood following release of insulin. Because different food groups can have an effect on the release of the insulin and glucagon, antagonistic hormones that regulate the concentration of glucose in the blood, different food groups can have a significant impact on energy level, mood, and long term ability to maintain glucose level balance. For example, eating a carbohydrate-rich meal leads to a rising blood glucose level and release of insulin which can lead to a significant drop in blood glucose levels as following the release of insulin body cells take up more glucose and liver stores glucose as glycogen. Other stimuli such as eating protein or fasting, can lead to release of glucagon which stabilizes blood sugar levels by raising them. High blood glucose levels allow for more energy to be available in the blood which is useful for athletic activities. In order to maintain alertness or mental functioning, maintaining a steady blood glucose level is helpful through the ingestion of protein.

Certain essential nutrients must be provided by the diet as the body can not make them on its own. These essential nutrients are nutrients typically in the form of vitamins and minerals. These nutrients can enter the body through food, nutritional supplements, or vitamins. Not having these nutrients can lead to the illnesses which must be treated with more expensive pharmaceuticals or surgery. Obtaining these minerals through a food is the most cost and time effective way to ensure adequate absorption and levels within the body. However, vitamins or nutritional supplements are still several times of magnitude less expensive than neglecting daily nutrition and requiring surgical or medical hospitalization to treat something acutely that could have been addressed with daily attention and discipline. However, the difficulty with some nutritional supplements is absorption and taking the right amount of vitamins in combination with the right foods to ensure the body is able to absorb the vitamins. Having an accurate log and recorded schedule as well as a record of nutritional levels of food can be helpful to ensure the proper amount of nutrients are being received from the diet and supplements in a timely way. It is important to avoid taking too much of certain vitamins as they have adverse side effects and can take significant amount of time to be removed from the body.

Utilizing these basic trends it is helpful to record an accurate diet log to plan for optimum blood glucose levels based on personal schedule needs. However, since everyone's response to foods is slightly different and their energy expenditures vary throughout the day, it is important for each person to be able to more accurately correlate their diet with their energy level over time. Often looking at these levels, on a meal-to-meal or even daily basis can vital data to understand and correlate blood glucose levels with diet. It may be easy to overlook the importance of a meal the night before for its effect to help stabilize blood glucose levels the next day. As well it would be easy to neglect certain small snacks throughout the day for their impact on blood sugar levels and consequently metabolism and energy level. By having an electronic storage data can be easily maintained and accessed and entered easily without significant amounts of time.

Further diet can have a powerful effect on mood and behavior that is often overlooked. Using a computerized system, effect of diet can be studied to ensure a steady baseline for optimal mental functioning. Further, the computerized system can help establish compliance as a means to determine its effectiveness as a treatment. In addition to blood sugar levels, metabolism can also affect cognitive function based on the level of nutrients in the diet, indirectly through energy level, as well as through the effect on hormone and neurotransmitter levels. Diet can most obviously affect sleep. Sleep can then affect hormone and neurotransmitter levels which can lead to chronic behavior problems. By systematically gathering and analyzing information about diet and energy levels through blood sugar levels, behavior patterns can be studied based on eating patterns and nutritional histories to help identify helpful foods and effective diets.

One of the greatest obstacles for any type of treatment for cognitive performance, behavior problems, or mood disorders is compliance with treatment plan. As a result, inexpensive solutions that require long term consistent efforts many smaller decisions each day are often overlooked for more expensive solutions like medicine that require less decisions to monitor each day. Having a computerized or automated monitor can remove the time consuming burden for a person to take meticulous notes or diligent entries. As a result, the importance of the chemical contents of food and the discipline of keeping a regular schedule can be used to provide treatment for many problems without the harmful side effects and unwanted by-products of powerful pharmaceutical products.

Most importantly, this systematic approach to measuring and analyzing food patterns can determine the contribution of time in eating patterns more effectively than without using a health improvement and diet history system. Time before meals, last meal of the day, frequency before meals, and consistent diet and eating patterns can be more easily factored in a result of consistently many meals over time. As a result, an easily overlooked factor which is not considered when meal planning or diet journals kept by hand such as time can be accounted for and provide valuable information that otherwise may not be considered when considering diet or calorie consumption alone. Time can be tracked using a sensor system that allows entries of calorie consumption, purchase, or ingestion to be recorded exactly at the time they occur or to allow a user key field where the time can be entered. These valued can then be studied for their effect on eating patterns, metabolism, weight gain, and overall health. Further, it may also be possible to use data gathering devices such as sensors attached to blood glucose monitors, blood pressure measuring devices, heart monitor, food thermometers, body thermometers, to enter time information at the same time as reading are taken and able to be entered into the health improvement and diet history system.

Metabolism is often overlooked factor in health improvement and weight management. It may be just as important if not more important to monitor energy expenditure, instead of just calorie (energy) consumption. Utilizing the Weir equation to compute energy expenditure per day or the respiratory quotient can be accomplished by tracking volumetric flows of Carbon Dioxide and Oxygen into and out of the body. A portable unit for metabolic analysis can be used to determine the partial pressures of oxygen, carbon dioxide, flow rate, temperature, and pressure. This information can then input directly into the overall system to better improve health and monitor diet.

Controlling blood sugar levels may be useful in stabilizing mood and behavior. Further, it has been that certain foods have additional positive effects on behavior. In particular omega-3 fatty acids have been demonstrated to reduce depression and anxiety. Additionally, it has been demonstrated that other foods can increase depression and anxiety. In particular, fried foods and oils from soybean have been shown to have a negative effect on behavior. By more carefully tracking diet, this invention allows the optimal effect of foods on health and behavior to be achieved and problems in the diet to be more easily identified.

In particular, it has been shown that diets rich in omega-3 polyunsaturated fatty acids is useful for reducing depression. Further, it has been shown that the presence of omega-6 fatty acids in a diet population is related to higher incidences of depression. More significantly, researchers have shown that there needs to be a proper balance between the omega-3 fatty acids and the omega-6 fatty acids in order to ensure reduction in depression. This finding demonstrates the need to be able track small amounts of nutrients consistently over time in a person's diet in order to understand the effect of diet on health. Secondly, this research also identifies the importance of being able to compare and analyze certain components of diet relative to one another. While calorie counting is difficult on a manual possible, it is not practical to be able to identify all of the significant nutrients and ingredients and collect them over time and analyze them using mathematical operations without the use of a computerized system, electronic data storage, or collection.

While various nutrients and food groups and ingredients are useful to improve health, they must be taken consistently over time in order to avoid more severe and drastic forms of treatment such as surgery or powerful pharmaceutical medications. Tracking and monitoring their intake ensures compliance as well as consumption at adequate levels to improve health and identify possible deficiencies or diagnose disease.

Nutrients in some cases must be taken in small amounts that are well below taste or observable threshold levels in some cases. The levels of these nutrients must be taken consistently. Secondly, the nutrient level is difficult to track based only on what appears on the package. Packages are difficult to use for record-keeping purposes. In addition, in some cases it may be necessary to perform a calculation of one nutrient level to another with multiple data points over long periods of time to identify a factor that affects health. It is not convenient or practical to perform these calculations at meal time. Additionally, the calculations may require collecting data over long periods of time with more than consumer for comparison. This is difficult to track by hand, tedious and not practical. However with electronic records storage and database calculation tools the information can be more readily entered, accessed, managed, and analyzed.

Additionally, certain foods have a dramatic effect on reducing blood sugar levels. This effect can have a profound effect on moods and diet effectiveness would not be noticeable by recording the calorie values alone. For example, cinnamon and balsamic vinegar have been noted to significantly reduce blood sugar levels. By reducing blood sugar levels cravings and feelings of hunger can be reduced without increasing calorie intake. These foods demonstrate the importance of recording additional information beyond calorie information. Further, these foods demonstrate the usefulness of additional information to plan menus based on the synergistic effects of foods to provide chemical components which can help balance the diet without relying on only calorie restriction.

Further, if the goal is to reduce weight rather than focusing on a decrease in calories it may be more effective to measure metabolic rate. Rather, than focusing on how many calories are accumulating in a diet, it may be more beneficial to monitor the rate they are consumed and focus on methods to increase this rate in order to achieve the goal of weight reduction.

The diet history of an individual can be easily obtained through the use of electronic equipment at the point of sale and analyzed using database software to not only improve compliance through reminder and accurate information, but also diet could easily be screened to identify signs of disease, risk factors, or diseases caused by nutritional deficiencies. Anemia, pellagra, and celiac disease may be more easily identified and controlled through the use of highly accurate and comprehensive diet monitoring.

Further, diet monitoring can also be used in times of life that require specific nutritional requirements. For example, during pregnancy it is very important to ensure the health of the mother as well as the health of the child. During pregnancy it would be beneficial to ensure the mother is eating foods with enough folic acid and prevent birth defects. The presence of folic acid has been identified to have significant benefits to reduce birth defects. Further, it is important to note that osteoporosis, improved mental and athletic performance can also be affected by making the necessary changes to monitor and improve diet. Small changes to diet can have a dramatic impact on improving health. However, without continuous attention to the diet the benefits of a disciplined diet can be overlooked. The invention provides a means to monitor important elements of the diet over time, so that beneficial aspects are not overlooked and critical deficiencies are addressed to protect against disease and more expensive acute corrective procedures.

Additional concerns that can be addressed through the use of diet are safety and reliability of food supply and regulations to protect global food supply. Notable product safety recalls have occurred in the food supply. While often times notice is limited to TV, radio, or newspaper in some cases, news may be not be able to reach consumers before the contaminated or recalled food is ingested or prepared. This diet monitoring systems would be able to receive information directly from food suppliers so that consumers would not have to watch or wait for the latest news report to confirm their food supply is safe before eating. Further, in the event that a recalled food is consumed and the corresponding package is thrown away before the notification of the food recall is received, the diet monitoring systems would provide accurate records that could be used to track and confirm that recalled food was purchased and consumed.

Further, pricing information is often transmitted on a weekly basis using weekly periodicals and newspaper circular. It is difficult for a typical consumer to process all of this information to determine what stores have the lowest prices for the most items to provide the effective and lowest cost and most complete shopping trip for an individual consumer. The health improvement and diet monitor would enable nutritional information and pricing information, so that a complete grocery list could be searched which meets both the dietary considerations and budget information for an individual consumer. The pricing as well as the nutritional information could be easily entered online and searched to save time without having to consult multiple newspapers or multiple trips to the store.

In addition, to nutritional information and food recall information, a consumer may choose to more easily select foods based on the food regulations and type of regulations that are in place to ensure food quality. The diet monitoring system could be more easily scanned to preselect foods on a grocery list based on their country of origin or the history of food manufacturer with recalls. Further, additional foods made with genetically modified components, carcinogenic preservatives, high amounts of pesticides, or imported foods from other countries could also be eliminated from the grocery list based on correlation of the brand name, the food manufacturer, and the food supplier. This would save time for the consumer having to scan shelves and read each label or travel to multiple stores. Further, it would be easier to support local produce, local food suppliers, local food manufacturers, with consistent with consumer's standards and products that meet the consumers budget, delivery, and nutritional requirements through the use of a systematic scan of databases of available food products with nutritional values and costs that are also searchable.

Another significant aspect of this invention is that it promotes health by saving time. Consumers will be able to act on the volumes of nutritional, safety, and pricing information as a whole and make plans to purchase, prepare, store, and consume foods based on their needs instead of responding to limited store offering with limited time. This program can track time in the grocery store to calculate the true cost of obtaining food from each particular store or a recipe, meal, or food basis. This will enable the consumer not only to save money on the purchase price of food, but it will more accurately record the true cost of obtaining, preparing, and consuming foods from a particular store or restaurant. This will be accomplished by entering a time in which the consumer enters the grocery store and the time the consumer exits with the purchased item(s). The purchased item(s) then will have a purchase time and a corresponding value for each time according to the amount of time spent to purchase each item. This will enable large bulk purchases to be compared more easily with single item trips to particular grocery store with low prices on specific items for example.

A computer system for entering health decisions included in a remotely compiled electronic statement into a personal account stored in a local computer system, comprising: a remote computer system made up of a remote processing device programmed to compile an electronic statement in an electronic data format processable by the local computer system. The electronic statement includes at least one health decision.

A health decision is any financial transaction that consumes time, money, or other resource and can affect health. A health decision consists of something one would consume such as a meal, vitamins, or medicine. A health decision could also consist of a physical activity such as exercise or a medical treatment. Each health decision may have more than one category code. Certain different activities like a food purchase or a physical exercise may be linked by a common health category code. In this example, these two would both have the same category code of calories. The food purchase may consist of calories contained in the purchase and the exercise may consist of the calories consumed in the exercise. Further, each food may consist of several category codes for the different food groups, minerals, and nutrients it contains. Each health decision includes at least one health category code.

A communication device is operatively coupled to receive the electronic statement from the remote processing device. The communication device electronically communicates the electronic statement to the local computer system via a communication medium. A local computer system includes: a storage device for storing health decisions in the personal account, and for storing a plurality of health supplier category codes, and categories. A first input device has a communicative coupling with the communication medium to receive the electronic statement. The input device is further coupled to the storage device to store therein the electronic statement. A second input device can receive categories input by a user.

A processor is operatively coupled to the storage device and the input device for fetching health decisions, health supplier category codes, and categories from the storage device. The processor is programmed to associate a health supplier category code with at least one category received with the second input device, and to store the health supplier category code in association with the received category in the storage device. The health supplier category code can also be supplied from a database of information. Further, the processor is programmed to receive the electronic statement from the remote computer system via the communication medium and to store the electronic statement in the storage device. Additionally, the processor determines if the health supplier category code included in the health decision is stored in association with a category in the storage device; and assigns the health decision to a category stored in association with the health supplier category code. The processor stores the assigned health decision in the personal account stored in the storage device.

Further, with using computer system that has access to database containing personal health history; database of diet history; database of cost of available foods; database of recommended diet plan; and database of travel and preparation time of available foods it would possible for an individual consumer to determine the true value of foods at any point time based on their health needs as determined by nutritional values, health, and dietary values.

Additionally, significant changes in diet, weight change, blood sugar, quality of nutrition or food intake could be more easily identified over time. This would also lead a more quantifiable way to prevent health problems and promote wellness so that food taken every day can have the maximum value and optimal effect on health.

It is an object of the invention is to use a systematic method to monitor and control diet to improve health.

It is an object of this invention to provide a more accurate method of measuring and producing change in food consumption and dietary habits.

It is an object of this invention is to provide a method of tracking nutritional information of food purchases and consumptions with changes in basic health data including weight change, blood sugar level, metabolism change, cholesterol, heart rate, blood pressure, enzyme level, blood alcohol level, antibody levels, iron level, response to food allergen levels, heavy metal level, etc.

It is an object of this invention is to provide a monitoring, storing, analyzing, and retrieving dietary and nutritional information which may have an impact on health.

It is an object of this invention is to provide an apparatus for accessing, compiling, storing, and tabulating diet information from the point of sale to the point of consumption.

It is an additional object of this invention to provide a method to more closely correlate the effect of food on health on an individual basis as well as using aggregate data.

It is an object of the invention to control the rate at which the food is consumed, purchased, released into the bloodstream, and affect health.

These and other objects of the invention will be best understood when reference is made to the drawings and the description herein below.

BRIEF DESCRIPTION OF THE DRAWINGS

FIG. 1 is a diagram 100 of typical flow of decisions and information that effect health.

FIGS. 5A and 5B are a view of Report from health improvement and diet monitor system.

Figure 1B:
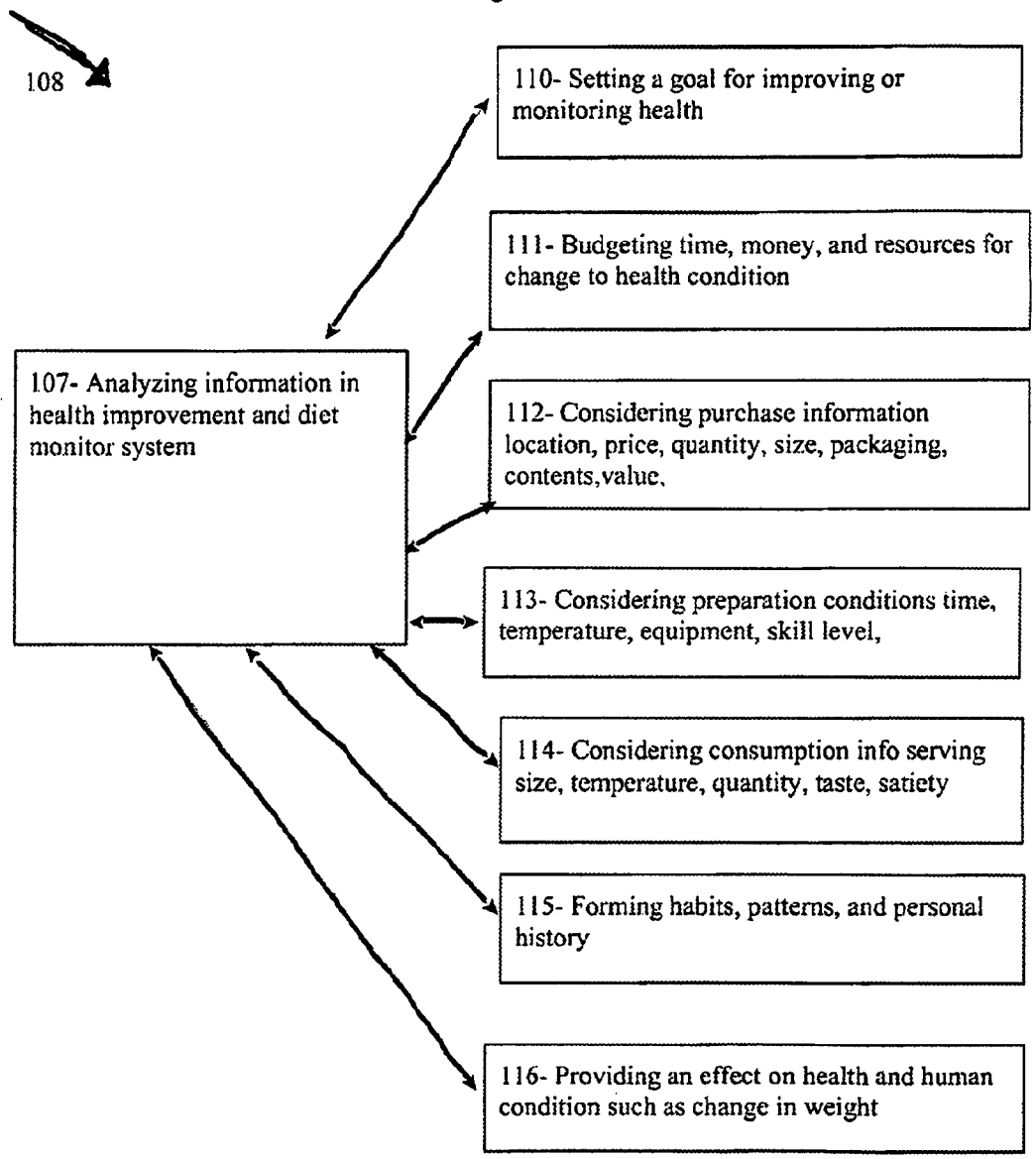
FIG. 1B is a diagram 108 of some of the process steps of the health improvement and diet monitor system.

The drawings will be best understood when reference is made to the description and claims which follow herein below.

DESCRIPTION OF THE INVENTION

FIG. 1 is a diagram of typical flow of decisions and information that effect health. In the typical decision making process found in the everyday diet and special diet programs time, money, and resources is spent on a decision which effects health condition 101. This could include paying for a diet program in the form of a book, membership fees for a weight loss program, or paying to consult a physician or other licensed health advisor. In other cases, this step may also include time spent reading health or articles on weight loss. This step may can in the form of a new year's resolution or a goal.

Purchasing health/food product based on its location, price, quantity, size, packaging, contents and estimated value 102 is typically the second step. This step also consumes time and money. This step typically follows sequentially from the first step but there is not necessarily any guarantee of information from 101 having any effect on 102. This decision may involve purchasing foods on a special diet program. This step may also include making food selections based on the consumer's own preferences or what health information the consumer quickly sees on the label.

Transporting, moving, storing, and preparing health/food product based on conditions time, temperature, equipment, and skill level 103 occurs in the next step. This step is affected by the decision in 102. However, there is no record or control to ensure that the activity in this step complies with the reason for making the decision in 102. Specifically, if a food was purchased for a dietary consideration such as low salt and the consumer adds salt to this when preparing previous steps 101 and 102 have little effect on the outcome of 103.

Serving and consuming health/food product based on size, temperature, quantity, taste, and satiety 104 is the step that follows. Although, this step can take place quickly and most often thought of when considering diet, this step is dependent of the previous three steps. This step is a direct result of the previous three steps and is limited to the amount of time and consideration that was put into the previous three steps.

Forming habits, patterns, and personal health and diet history 105 follows directly from the previous four steps. Long term health consequences are caused in this step. Further, this step may be affected by both long and short term considerations. This step is the least considered and has a significant effect on overall health.

Providing an effect on health and human condition such as a change in weight 106 is the final step. This step is the culmination of the decisions made in the previous five steps. This step is generally more easily observed based on the physiological and psychological change which it produces. Examples of this effect may be a change in weight or a blood pressure reading. There are a total of six steps, however, the outcome of this decision is typically considered most when making evaluating any of the previous steps. Generally, it may take a considerable amount of time for the results of the previous decisions to produce a consistent and noticeable effect on this step.

As a result, due to the considerable time that takes place between the first and last step, it is difficult to affect changes in the earlier steps and the overall process based on the outcome of this step. Information is not available quickly enough or in sufficient detail to positively affect the earlier decision steps and to produce the desired result.

FIG. 1B is a diagram 108 of some of process steps of the health improvement and diet monitor system. A method for improving health and monitoring health comprises the following steps: setting a goal for improving or monitoring health 110; analyzing information in health improvement and diet monitor system 107; budgeting time, money, and resources for making a change to health condition 111; analyzing information in health improvement and diet monitor system 107; considering purchase information location, price, quantity, size, packaging, contents, value 112; analyzing information in health improvement and diet monitor system 107; considering preparation conditions time, temperature, equipment, skill level 113; analyzing information in health improvement and diet monitor system 107; considering consumption information serving size, temperature, quantity, taste, satiety 114; analyzing information in health improvement and diet monitor system 107; forming habits, patterns, and personal history 115; analyzing information in health improvement and diet monitor system 107; providing an effect on health and human condition such as change in weight 116, and analyzing information in health improvement and diet monitor system 107. Information can be sent to the health improvement and diet monitoring system where it can be analyzed as part of 107. The health improvement and diet monitoring system 107 contains electronic storage media, database, modules, and communication means for accessing this information at a later date and comparing it to existing sources of information. The health and diet monitoring system can record and transmit this information to other steps and be used as a reminder and to analyze subsequent steps for compliance with this goal in 110. Information entered into this step can be analyzed in health improvement and diet monitor system before, during, and after each step of the process. This enables goals to be considered often and information such as previous purchase decisions, responses to health in response to previous health decisions, and other important decisions to be considered before decisions are made.

Figure 2:
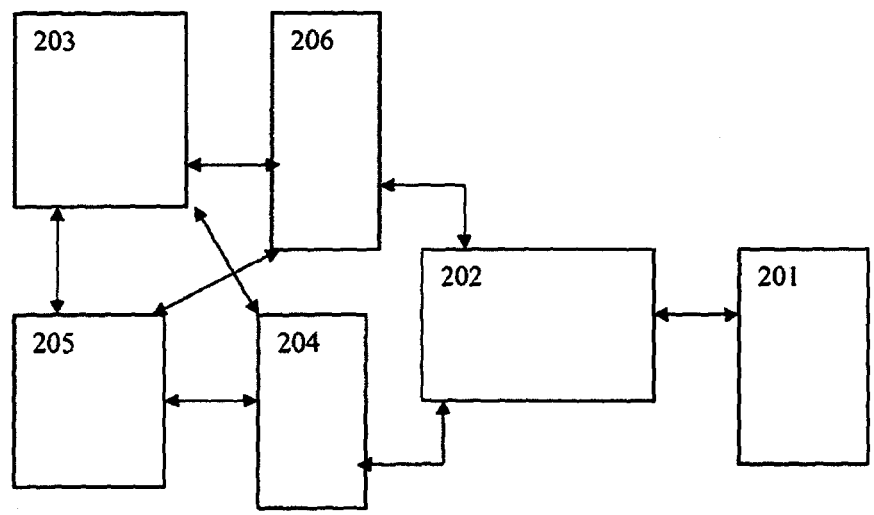
FIG. 2 is a diagram of the health improvement and diet monitor system.

FIG. 2 shows a schematic of the system according to the invention. It is to be understood that the system is using a computer as a network site. The hardware will be configured and customized by various software modules. The software modules will include communications software of the type used for Internet communications and a database management system. The software modules may include additional communications software to receive information from other communication sources such as telephone, PDA, etc. Any number of commercially available database management systems may be utilized to implement the invention. Those of ordinary skill in the art of database management application programming will be able to make and use the invention according to the disclosure hereof.

A process control unit 202 is connected to a search engine 206 and a health management/food monitor unit 204. The process unit 202 is also connected to a communication port 201. The user accesses the process unit 202 via the communication port. The communication port may be a keyboard or a mouse accessible from a home computer. The communication port may also be a telephone or cash register at the grocery market. Other examples of the communication port include RFID, I/O technology, WIFI, Bluetooth, etc. Additional communication ports may include sensor or automatic data retrieval ports including those interfacing directly with a scale, weight sensor on a chair, bar code scanner, thermometer, blood pressure, or pulse monitor. The search engine 206 is connected to a food base 203. The search engine 206 is also connected to a health history/diet monitor 205. The health management/food monitor 204 is also connected to the food base 203 and the health history/diet monitor 205.

The process unit 202 will manage the flow of information through the system. A communication port is provided to allow access to the system through communications with other computers connected to the network. The network may include any number of external computer systems or access through local and wide area network to other connected computers either directly or through routers, modems, broadband, or DSL. The system will include database memory 203 to store the food base. The food base may be in the form of a data file comprised of a plurality of sets of information. Each set of information will correspond to a particular food available for purchase. Each set of information will include a number of predefined fields containing search parameters and additional types information that is considered when making a food purchase such as cost, size, preparation and storage requirements, contents, calories, nutrient, food allergens, meals, country of origin, background information on the manufacturer, shelf life, storage time, lot #, information on related food safety recalls, and other information on the foods on diet that may have an effect on diet or health.

The data records on foods can be established so that each food can be cross-referenced and identified by one or more meals and the contents or characteristics which make it up. An example of breakfast meals may include: omelet, cereal, yogurt, toast, egg—hard boiled, oatmeal, and banana. Each food parameter field may be organized by storage location with the desired amount of detail. In addition, each food will have a complete listing of nutritional information which currently appears on most food products. These fields will include. An example is included as FIG. 2. For a shopping search, it may be convenient to search by city, zip code, or distance from home. For a home search, it may be convenient to specify by room, pantry shelf, or section of the refrigerator.

If a relational database management system is utilized, it would be advantageous to relate the location field of the food to a location database file which will include relevant information, such as accessibility (operating hours), inventory turnover rate, capacity or storage space available. A location database file may include information on stores such as closest location, stores with best average price for a grocery list, lowest prices, or best selection. It would also be advantageous if an inventory management tool were utilized to automatically update the food base or the location database file when food is moved from one location to another. Additionally, it may be advantageous for the food base 203 and the health management/diet monitor 204 to interact and update each other.

Finally, the food base 203 will include some security or password fields which will specify who may have access to the food records for the purpose of updating, inventorying, editing, maintaining, and deleting food records.

The system may also include memory which stores a health history/diet monitor base 205. The health history/diet monitor base 205 will be a database file which will be customized to each user's purchases or consumption of foods from the food base 203. A specific set of information will be accessible to users and information will be operable for a variety of queries and functions. The system also includes a health management/diet monitor 204 which manages the submission, manipulation, and operation of health history such as weight, calories consumed, resting heart rate, metabolism contained in the health history/diet monitor 204 and food records contained in the food base 203 such as price/food, calories/food, protein/food, etc. The system will also include a search engine 206 which handles searches to the health management/diet monitor 204 and food base 203. The operational features of the search engine 206 are described below. The health management/food monitor 204 and the search engine 206 may be implemented through commercially available database management systems. Other conventional search and query capabilities may also be used to search the databases.

A user may access the system using the communication port 201 with a variety of screens and choices. A user may be able to receive and information through a variety of interfaces. In one preferred embodiment, communication by the user may be achieved through html pages. In another preferred embodiment, the user may be able to submit and receive information using a telephone. In another embodiment, information may be updated using information transmitted from cash register at grocery store or handheld scanner at grocery store before purchase. In another embodiment, a monthly consumption and purchase log based on cost, nutrient level, and correlation to prospective goal may be displayed, printed, or recorded at a predetermined time interval to track progress on a monthly basis for example. In addition, this nutrient record may be provided alongside a grocery list.

Information transmitted to the system will most likely be from computer communications from individual users or consumers or food manufacturers or food stores. Any user who is not a food supplier or seller will be treated as an individual user or consumer. Food suppliers will be able to transmit inventory, pricing, and nutritional information concerning food. Individual users will be to transmit personal purchase and consumption of food purchases and receive tabulated sets of this purchase information over specific periods of time from the health history/diet monitor database 205.

An authorized food supplier may be able to upload significant amounts of information such as nutritional information or up-to-date pricing and inventory availability information. Optionally, a consumer may be able to access or submit this information. Optionally, the food supplier may be able to transmit information to the food base 203 or health history 205 based at the time of purchase by an individual consumer to the individual consumer's health history/diet monitor 205. Food suppliers and individual users may be provided "write access" to the food base or health history/diet monitor 205 through some identification or verification protocol. A password system or source terminal identification number may be utilized to verify authority for "write access". Each consumer account will have its own password for changing or updating information.

Once a consumer chooses to search for a particular food or meal from the food base, he may have an option of searching the food base 203 based on type of meal, type of food, cost, a food high in a specific nutrient, preparation time, protein %, carbohydrate %, or a combination of any or all of these criteria. The consumer may also choose to select the health history/diet monitor 205 for a specific meal consumed on a specific date or for a type of food that has not been eaten recently. Additionally, the user may query the food base 203 for a complete grocery list based on a specific diet or training program found in health management/food monitor unit 204. The food base 203 can output a grocery list that is currently updated to show which items are available at the home and what items must be picked up at the store. The food base 203 would also enable a specific grocery list to be searched completely for the lowest cost at local grocery stores to show foods that fit within budget or calorie/nutrient allotment.

When searching, a user may search for an entire diet, a meal, a food, a calorie, or nutrient over a specific time period. The complete list of available search fields may be presented to the user in the form of a table or list. The complete list of available search options may be presented to the user with a scroll bar window. Additionally, a key word search may also be used in the various fields. Further, it may also be possible to search by cost, brand name, common name of the food, or UPC symbol. It may also be possible to search using a scanner to scan in specific UPC codes or other scanner readable bar code to more quickly search for and update available inventory in the food base 203. Using a scanner would be able to provide information for additional fields without requiring additional keyboard input. Further, based on the restrictions supplied by the user in health management/food monitor 204 only certain foods may be searchable in order to restrict the diet or promote certain foods in view of specific plan or program that is loaded into the management/food monitor 204.

When an authorized user accesses the food base 203, a search may be used to locate an individual food or a group of food records such as a diet plan or a recipe or a complete list of meals for a week. However, the user may not have complete write access to modify the records in the food base. It may be possible for one member of the household to restrict write access and apply certain restrictions from the management/food monitor 204 over the entire food base 203 for all users of a particular household. The records in the food base 203 may be presented in a format and modified by the user. The user may elect to delete food records based on convenience and preferences. Further, the user may only allow certain information from specific food suppliers based on cost, distance, or previous experiences with the specific food supplier.

A user may have the option of searching for an entire diet, meal, food inventory, or recipe on the system. By selecting the option to retrieve records, the process control module 202 will instruct the health history/diet monitor 205 to retrieve all foods consumed over a given period of time. It will be possible to see how closely a given user profile of actual foods consumed matched with a prospective diet. It will also be possible to retrieve a specific data value based on specific foods consumed over a given time period. For example, total calories consumed or average protein: carbohydrate on a daily basis could be determined as well as amount of calories consumed before 7 PM will also be able to output over a given time period to evaluate food consumption, list of foods consumed, basic analysis of nutrients consumed, correlation of foods and nutrients consumed with health factors such as blood sugar level, blood pressure readings, energy level, or weight gain.

As an alternative to being accessible only online to access health history or monitor diet compliance, it may be possible to update the system including both the 205 health history/diet monitor 205 and the food base 203 with at the point of sale at restaurants or grocery stores and to further correlate grocery store purchases with a home sensor and scanner when various foods are prepared, consumed, or thrown away. The system would work similar to credit card purchases where the individual purchases can be correlated with their nutritional information into a database that could be accessed to update the health history/diet monitor 205 and the food base 203 remotely. Further, it may be possible to access the health history/diet monitor 205 and the food base 203 remotely with a telephone or PDA to enter information using a numeric code corresponding to the code of each item which would then correspond to the nutritional and price information for each item found in the food base 203. Finally, it may also be possible to receive information from health history/diet monitor 205 to a cell phone to provide suggested food selections when dining at a specific restaurant or to receive a grocery list as a text message from the food base 203 when shopping at a grocery store. The health history/diet monitor 205 and the food base 203 can also be set up to provide automatic reports to the user on a pre-determined time schedule such as a weekly grocery list set each Thursday or diet report including % of targeted calorie consumption achieved so far.

A user is presented with a table or list of options when the user accesses the system. The options will include submitting a food purchase or consumption to the health history/diet monitor 205, searching the food base 203, or searching the health history/diet monitor 205 or submitting or deleting a food or field for a food in the food base 203. The option of searching the health history/diet monitor 205 may be restricted to certain users who subscribe or have access to this portion of the service.

When a user selects the option of adding a food purchase or allowing access to a food supplier's products, the process control unit 202 submits commands to the health management/food monitor unit 204 which in turn passes information for the fields of the specified base from the user's computer through the communication port into the selected database record. The health history/diet monitor 205 is an electronically stored database. The health history/diet monitor 205 is a collection of foods stored in electronically readable memory. The records in the food base 203 will advantageously include the following information in the fields: brand name, serving size, calories per serving, protein USRDA % and weight, carbohydrate USRDA % and weight, fat USRDA % and weight, fiber USRDA % and weight, nutrients, vitamins, price history, consumption history, current inventory status at home and in store, and other information that the user may specify to be extracted from the food purchases in health history/diet monitor 205 and the food options in the food base 203 based on the program and specified values required from modules supplied in the health management/food monitor unit 204. The user may also be able to indicate personal preferences following purchase or consumption in the health history/diet monitor 205 such as favorite meal, the meal served at last birthday party or family event, so that this information is accessible and readily searchable in the food base 203. Access may be restricted by including a field in the health history/diet monitor 205 identifying users which will not be granted access to the health history/diet monitor 205 even though they may have access to the health history/diet monitor 205 or by a fuzzy logic inquiry into the food supplier field.

It is to be understood that the system is not limited to using the physical file, record, and field structures described herein and other physical structures which are logically equivalent will be equivalent for the purpose of this invention.

The interactive search engine 206 will be invoked when an applicant-user selects the food search option from the opening table or list of items. The interactive search engine 206 may present a number of different visual representations to organize search options such as a scroll bar menus. Predetermined options corresponding to available entries for the various fields are then presented as a table or a list. The user selects entries from the options presented. Certain fields may be searched using key words or literal string inquiry. The initial search indicates the number of records which satisfy the search. If a plurality of records is found, additional iterations of the search may be run successively. Each of the tables or lists will be represented, this time, however, only the entries indicated in the previous iteration are displayed. Additional inquires may be submitted iteratively and the search selections can be narrowed. When the search selection narrows to meet the preference of the user, the user may select predetermined portions of the selected records. The user may then be presented with the option of seeing a diet that matches contains the selected record or starting a new diet that contains this selection based on the food choice or specific nutritional breakdown. The diet can be designated for a specific time period such as a three month period or monitoring can be set up over a longer period. Additionally, a specific dietary requirement can be applied such as calorie restriction over an extended time period and the search option will search for foods that meet that requirement over the chosen time period.

If a user selects the health history/diet monitor 205 option, the system may use the iterative search engine to query diets and meals that match or fall under that specific diet or specific limitation being searched for. The search may be a subset of meals consumed over time in the health history/diet monitor 205. They also may be designated by the presence of output of special health values such as weight, change in weight, blood sugar, blood pressure, cholesterol, or metabolism readings for the specific consumer. According to this feature, food suppliers may be charged for access to this information in a tabulated form. The charge may be imposed as a basic subscription charge which will entitle a food supplier to a predetermined number of searches. Various other access arrangements may be used to utilize valuable information of the choice of foods and the effect of foods over time on various parameters of health.

Figure 3:
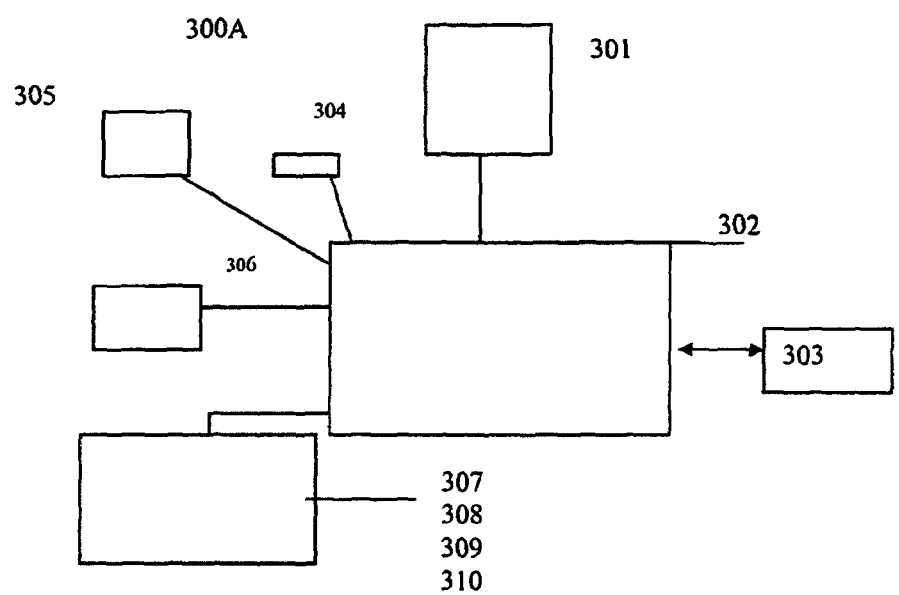
FIG. 3 is a diagram of conventional computer system which may be used with health improvement and diet monitor system.

FIG. 3 is a view of health improvement and diet monitor system showing a block diagram of conventional computer system which may be used with health improvement and diet monitor system. The remote source 301 may be an online hosting service which allows the computer 302 through a modem to access the internet and gain important information. The computer has a removable storage device 303 such as removable hard drive, a disk drive, or USB storage device which may be used to remove records or program file from the health improvement and diet monitor program. Data such as blood sugar levels, high blood pressure, weight, temperature, cholesterol readings, may be entered into the computer via data sensor 304. The data sensor 304 may be connected to the computer directly or they may be able to transmit information to the computer via an internet connection. Data can also be entered into the computer concerning food and health information via a keyboard/mouse 305. Additionally, a bar code scanner apparatus 306 may be used to scan information into via food purchases, meal consumptions, or other health events with predetermined identifiers or values. The computer can execute programs such as the health improvement and diet monitor computer program 307. The computer program 307 may contain features such as a personal account 308, personal calorie counter 309, and personal protein counter 309.

Figure 4:
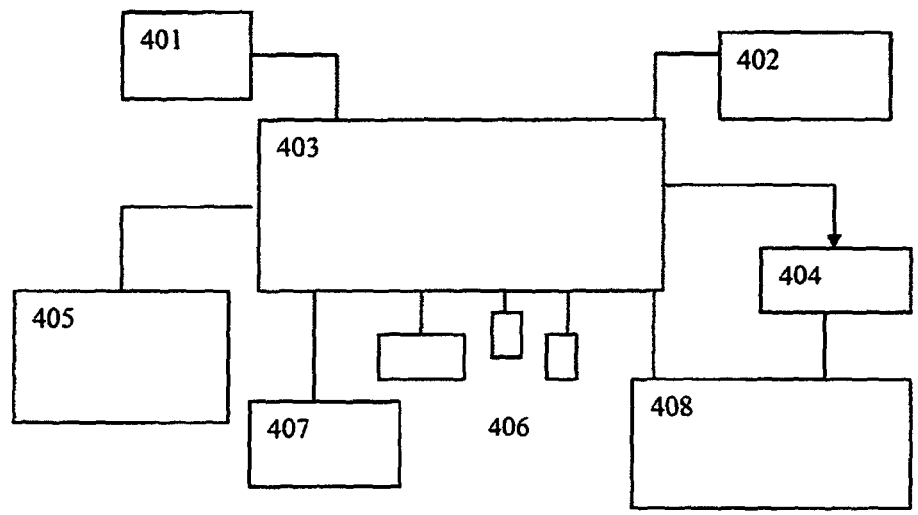
FIG. 4 is a flow chart illustrating the flow of information from an electronic statement into a personal account according to the invention.

FIG. 4 is a view of health improvement and diet monitor system illustrating the flow of information from an electronic statement into a personal account according to the invention 400.

The food nutritional information 401 is contained in a database.

The food supply, location, and pricing information 402 are found in another database. The process controller 403 is able to search the database and compile values for keyword searches that are implemented in the process controller. The Diet Consumed is compiled in another database 404. This information is correlated to the values in the other database to provide a nutritional and price running log and total for the foods consumed. Additionally, health and disease information may be associated with the nutritional and diet information 405 compiled. Health Program/Goals Modules containing specific program, diet, or goals may be found in 407. Additional, programs based on diet books or tailored programs to the health history may be entered as a program module 407.

The comparison of diet and health received and analyzed values can be output into a compliance record 408.

Figure 5A:
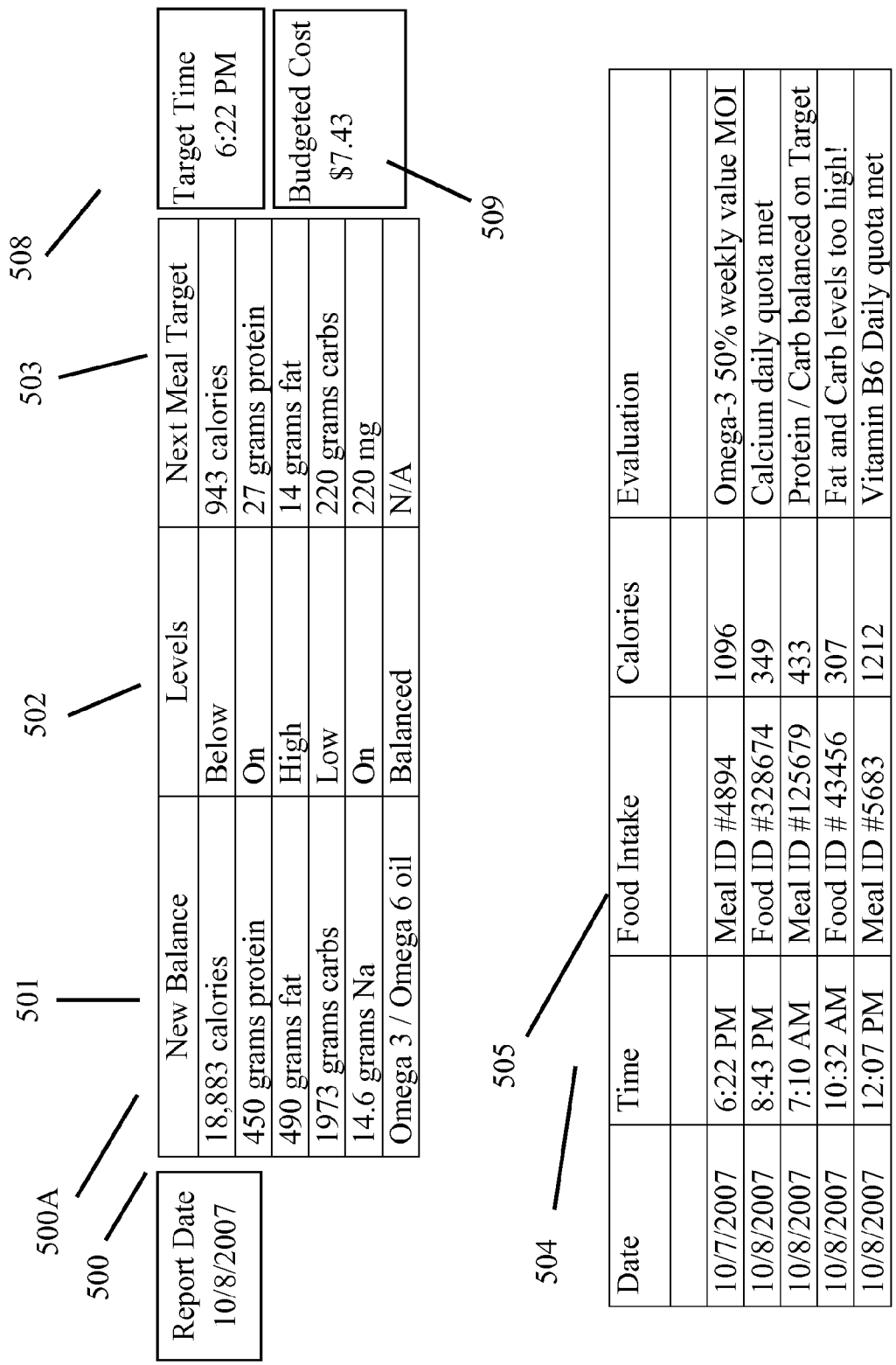

FIGS. 5A and 5B are a view of Report from health improvement and diet monitor system. Sample report from health improvement and diet monitor system 500 including numerous standardized output values as well as customized feedback and time stamp for further consideration of the data to provide Time stamp for Food intake 504. The running Total of Nutritional Values is displayed in a table format 501. Sample output categories include calories, protein, fat, carbohydrates, and mineral levels such as sodium (Na) for example. Further, mathematical operations can be performed on these data values to provide additional indications of nutritional level and health status. In this example, the ratio of Omega-3/Omega-6 levels can be recorded and output. A simple evaluation feedback mechanism is provided in 502 to assess the level based on goals for the specific targeted nutritional values and indicated time intervals. For example, these values could be set to provide an average output for each meal, day, week, or month. The Levels output 502 can then be used to update the status of reaching the particular goal.

Further in FIGS. 5A and 5B, based on the established goals and the running total of nutritional values the next meal target could be provided in terms of suggested nutritional values as shown in Next Meal Target 503. Further, based on program goals and other established inputs such as schedule, glycemic index of foods, the foods available in pantry, and the target time 508 for the next meal could also be output. The budgeted cost 509 for the next meal could also be output based on established program goals as well as in combination with a running total of food purchase costs that is also able to calculated, stored, and accessed in the health improvement and diet monitor and output in the Report 500. Further, the budgeted cost 509 can also be used as a parameter along with suggested nutritional values for the next suggested meal 507. Each food would be able to be assigned a Numeric Identifier 505 which would allow it to be referenced and accessed from the database. Each food intake event would be evaluated for its significance towards moving away or moving closer to the overall goal. This evaluation 506 is seen to the right of the Food Intake 505. The evaluation 506 may be in terms of nutrient levels, protein and carbohydrate balance, or use of nutritional data in relation to other input data towards overall health and diet goals.

In one embodiment of the present invention, the next meal target meal is based on the diet intake that the user wants to control or improve. Such diet intakes include but are not limited to blood pressure, gluten free, specific caloric intake, carbohydrate to protein ratio, low fat, budgeted cost, etc. The user enters one or more intake parameters into the computing device. The user may define specific rules for the desired diet parameter. Such diet parameters may be predefined by software. The rules may be defined by existing desired parameters such as but not limited to Zone Diet, Weight Watchers, Celiac diet, low sodium diet, etc. The rules allow the system to calculate the nutritional values and provide the user with the requested information dependent upon the rules of the desired parameters. Such dietary goal nutrient values identify the nutrients to be consumed by the user to meet the dietary goals. In one embodiment, the dietary goal nutrient values define the nutrients and the quantity of the nutrients to be consumed by a user during a predetermined time period. For example, the dietary goal could be based on a daily consumption, weekly consumption, or monthly consumption.

One embodiment of the present invention stores multiple food items with the specific nutrients, calories, vitamins, minerals, and additional nutrient contents of a food item. The nutrient content of a food item may be determined by the nutrients of pre-made meals, foods, etc. The user may also enter the nutrients of a specific item manually. The user may also input or upload a recipe with the specific ingredients. The system would then determine the nutrient content of the food item by calculating the ingredients of the food item. The user may also enter the ingredients of the food item as the user prepares the food item.

To input the ingredients of a particular food item, the user enters the specific ingredient manually or uses a bar code reader. Other methods of entering the ingredient may be used. The user also enters the amount of the ingredient needed to prepare the food item. One embodiment of the system also stores the prices to purchase the particular food items and ingredients. These prices may also be increased by the costs associated with obtaining the particular food items and ingredients to calculate the total costs of acquiring the food items and ingredients.

For example, in one embodiment, a user enters the diet parameter that the user desires to meet. As described above, the user may select a particular diet plan, such as Atkins diet or Caveman diet, that contains the specific rules for meeting the requirements of the diet plan. The user may prepare a meal, including but not limited to breakfast. The user may, in one example, have eggs and toast for breakfast. The user would input the number of eggs, any ingredients added to the eggs, such as salt, pepper, cheese, etc., bread, and any additions added to the bread, such as butter and preserves. The user would enter the codes associate with the specific items consumed. The system then determines the nutrient content of the consumed items. To determine the nutrient content, the system may search databases, storage, online sources, or other sources for such items to obtain the nutritional information of the items.

The system calculates the nutrient content of the consumed items, such as total fat, calories, protein, vitamins, minerals, etc. for the specific meal based on the selected diet to determine the consumed nutrient value. The system then determines the Next Meal Target by following the rules of the diet. For example, the system may review the recommended nutrient intake for a determined period of time, such as a daily recommended nutrient value. The system compares the dietary target nutrient value to the consumed nutrient value to calculate a next meal target nutrient value. The system determines the nutrients to be consumed and the target nutrient values to be consumed. The system identifies the nutrients to be consumed to meet the dietary goal to allow the user to select at least one nutrient. Such a selected nutrient may be a nutrient that the user wishes to consume. The selected nutrient may also be a nutrient important to the diet.

The user can select one of the nutrients identified as nutrients needed to be consumed. The next meal target nutrient value of one embodiment is calculated by subtracting the consumed nutrient value from the dietary target nutrient value. The system may adjust the next meal target nutrient value due to the number of meals remaining in the predetermined time period. The system then displays food choices such as one meat, one starch, and one fruit to the user to select the items for their Next Meal Target wherein the food choices have the nutrients needed to be consumed.

Figure 6:
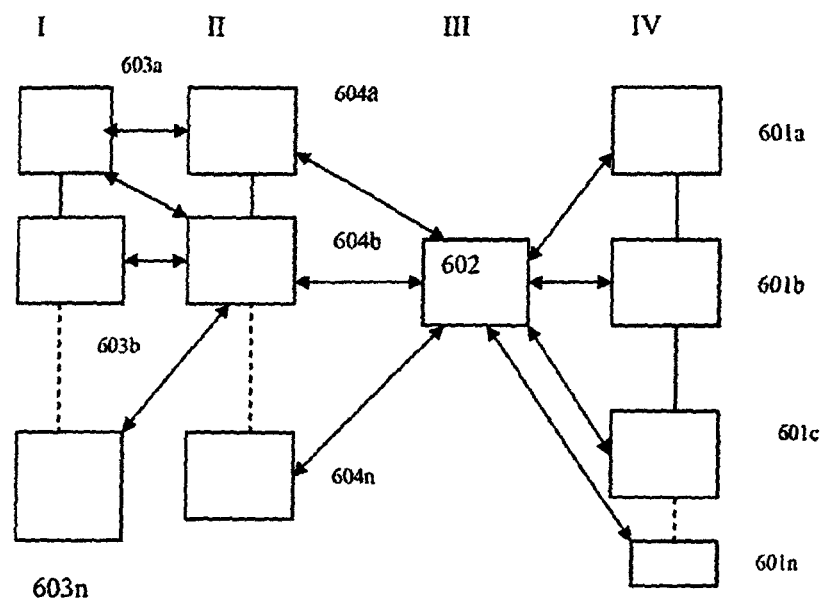
FIG. 6 is an environmental view of one embodiment of the present invention.

FIG. 6 is another embodiment of the invention. A plurality of I/O devices 601a, 601b, 601c, . . . , 601n are shown to the right of the control 602. The I/O devices may be a computer, keyboard, scanner, or a variety of wireless devices including Bluetooth, telephone, radio, RFID, or other remote devices which can transmit and receive signals with the control 602 without being directly attached through a cord. An input can provide information on food purchase, storage, or consumption. Additional inputs may include food temperature during storage or preparation or food weight. Additional sources of information can be vital health information linked such as height, weight, blood pressure, cholesterol, or memory tests. The input can be passive or active and provide qualitative or quantitative information. The information can be obtained in a continuous or passive manner such as from a weight scale attached to a door mat or the information can be obtained by a subject entering in subjective information such as rating the pain they experience on a given day on a scale of 1-10. Other inputs can be MRP information from RFID tags or by scanning in bar code information. Information can also be obtained based on scanning chips present in small amounts of food that have already passed through the digestive system for a more accurate tracking system of food consumed.

The I/O may include sensors for recording time or physical activity. In one embodiment, they may record the time a person spends in the grocery store actually purchasing food items. In another embodiment, they may record the time spent preparing food and transporting food.

A variety of processes can be carried out by expert systems 604a, 604b, . . . 604n. The expert systems interact with the databases 603a, 603b, . . . 603n. The databases may store a variety of information including food purchase information, food nutritional information, diet information, and health information. Additionally, the databases may store home food inventory, store inventory, and other material resource planning information. A database may include a prospective menu for a specified time period. The database may include the foods and raw materials for a particular menu. The databases may be updated on a continuous basis. The database may also include the most up-to-date sales prices for a particular grocery list. The expert systems may correlate food information to assemble diet information to provide health information. For example, the expert system may correlate the amount of nutrients consumed to nutritional deficiencies to identify potential health risks, allergies, or illnesses. The expert system could be in the form of a diet module of the person's choosing or a dietician's review of their nutrient intake. Information can be used to track the food purchases by a person over time which will provide a diet history of the nutrients they have likely consumed over the same time period.

In one embodiment, the expert system may be able to generate a grocery list by comparing a current home inventory list with a menu item. In another embodiment, the expert system may be able to compare the price of a grocery list at more than store to find the lowest cost for a complete grocery list. In another embodiment, the expert system may be able to calculate the true purchase cost of a specific food item or an entire list based on the time spent in the store purchasing the item as well as the expense for preparing and transporting the food. Additionally, the expert system may be able to calculate the cost of food based on additional metrics such as cost/weight, cost/calorie, cost/lb, cost/protein, cost/nutrient, cost/(calorie of a specific nutrient), ie cost/units of vitamin A, cost/lb of Omega 3 oil. In this way a more accurate cost of a person's diet can be approximated with each person and over long periods of time.

The ability to record, access, manipulate, and analyze information concerning a person's food purchases provides an easier method to budget, diet, and monitor and improve health based on food choices. The information can be obtained without requiring time intensive effort to record by hand or paper alone. Additionally, because more data points can be taken the information provides a more thorough and comprehensive pool of information which can be used by medical experts or by an individual at the time interval of their choosing closely associated to their yearly check-ups or weekly goals. The sensors and processor can provide the ability to gather and process information to provide a more thorough picture of a person's health through an accurate record of their diet and a more precise analysis of the balance of nutrients.

In one embodiment of the present invention, the computing device may accept input from the user identifying a specific nutrient that the user desires to consume. In another embodiment, the computing device may review the user's dietary goals and compare the goals to the user's recent diet. The computing device then identifies the nutrients which the user needs to consume to meet the user's dietary goals. The user then selects at least one of the nutrients identified by the computing device that the user desires to consume.

The user then identifies at least one type of food that the user desires to consume. The computing system then identifies the different brands and types of the food. To identify the different brands and types of the food, the computing device may search the user's recent purchases, food items that the user possesses a food item database, and/or a grocery database. The user then selects the food item(s).

The computing device searches the stores at which the food item may be purchased. The computing device also identifies the price at which the food item may be purchases. In one embodiment, the computing device determines the retail price of the food item. In another embodiment, the computing system calculates the price of the food item as the time required to purchase the food item and the costs associated with acquiring the food item, such as gas mileage, etc. The computing system then determines the amount of selected nutrients found in the food item. The computing system then calculates the cost per nutrient associated with the food item. The computing system displays this cost per nutrient to the user to inform the user of the cost per nutrient of the selected food item and the selected nutrient.

In one embodiment, the user may select multiple food items, which may include different brands of the same type of food or different food types (peanut butter compared to salmon). The computing system displays the results to the user informing the user of the costs per nutrient of the selected food items and selected nutrients. With such information, the user can decide which food items to purchase based upon the costs of acquiring the selected nutrients.

In one embodiment, the system calculates the costs required to purchase the food items to be consumed. The costs to prepare a meal may be adjusted according to the items that the user has in his/her possession. For such an embodiment, the system maintains inventory of the items that the user has in his/her possession. Because the user has particular items in possession, the costs required to obtain the items will be reduced because the user already has the items. The system may calculate the costs of acquiring the item as $0 (zero dollars) due to the fact that the user already possesses the needed item(s). Due to the need to maintain an inventory, the system will require tracking of the items purchased, gifted, acquired, or otherwise possessed by the user. The system will need to know the name of the item and the quantity of the item. The system will also need to track the usage, consumption, disposal, gifting, and/or removal of an item from a user's inventory.

In one embodiment, the system may designate these items as already in the user's possession. These items may be visualized in a special manner to highlight the fact that the user has the items in his/her possession. If the user does not have sufficient amounts of the item, the system will calculate the costs required to obtain the additional amount of the item needed. Such costs will include the price of the item and the costs required to obtain the additional amount such as gas, travel time, etc.

While the invention has been described and shown in connection with the preferred embodiment, it is to be understood that modifications may be made without departing from the spirit thereof. The embodiment described is by way of example and should not be construed as limiting of the claims except where referenced to the specification is required for such construction.

LIST OF REFERENCE NUMERALS

100 Process steps
100A Time from first to last process step
101 Process step of spending, time, money, and resources for decision which affects health condition
102 Process step of purchasing health/food product based on location, price, quantity, size, packaging, contents, and estimated value
103 Process step of transporting, moving, storing, and preparing health/food product based on conditions, time, temperature, equipment, and skill level
104 Process step of serving and consuming health/food product based on size, temperature, quantity, size, and satiety
105 Process step of forming habits, patterns, and personal health and diet history
106 Process step of providing and effect on health and human condition such as change in weight
107 Process step of analyzing information in health improvement and diet monitor system
108 Process steps
110 Process step of setting a goal for improving and monitoring health
111 Process step of budgeting time, money, and resources for change to health condition
112 Process step of considering purchase information location, price, quantity, size, packaging, contents, and value
113 Process step of considering preparation conditions, time, temperature, equipment, and skill level
114 Process step of considering consumption info serving size, temperature, quantity, taste, and satiety 115 Process step of forming habits, patterns, and personal history
116 Process step of providing an effect on health, and human condition such as change in weight
200 View of health improvement and diet monitor system
200A Diagram of Health improvement and diet monitor system
201 Communication port
202 Process control unit
203 Food base
204 Health management/food monitor unit
205 Health history/diet monitor
206 Search engine
300 View of health improvement and diet monitor system
300A Block diagram of conventional computer system which may be used with health improvement and diet monitor system
301 Remote source
302 Computer
303 Removable storage device
304 Data sensor
305 Keyboard/mouse
306 Bar code scanner apparatus
307 Health improvement and diet monitor computer program
308 Personal Account
309 Personal Calorie Counter
310 Personal Protein Counter
400 View of health improvement and diet monitor system
400A Flow chart illustrating the flow of information from an electronic statement into a personal account according to the invention
401 Food Nutritional Information
402 Food Supply, Location, and Pricing Information
403 Process Controller
404 Diet Consumed
405 Health and Disease Information
406 Data Acquisition Sensors
407 Health Program/Goals Modules
408 Diet and Health Received and Analyzed Values
500A View of Report from health improvement and diet monitor system
500 Report from health improvement and diet monitor system
501 Running Total of Nutritional Values
502 Assessment of Running Total of Nutritional Values
503 Next Targeted Meal Values Based on Running Total and Assessment of Running
504 Time Stamp for Food Intake
505 Food Intake with Numeric Identifier
506 Specific Nutritional Value Evaluation of Food Intake Event
507 Next Suggested Meal
508 Next Targeted Meal Time Based on Goals and Program
509 Budgeted Expense of next meal
601a First I/O
601b Second I/O
601c Third I/O
601n nth I/O
602 Control
603a First Database
603b Second Database
603n n-th Database
604a First Expert System, First Process
604b Second Expert System
604n nth Expert System

I claim:

1. A method for monitoring a user's diet with a dietary goal and providing a user with the cost information for purchasing a meal per a budget, the method implemented on a computer system with instructions stored thereon having an input device, the method comprising:
the computer system accepting a user input from the user with the input device, the user input related to a food intake by the user;
the computer system identifying a nutrient value associated with the food intake;
the computer system summing the nutrient value of the food intake consumed during a determined period of time to calculate a consumed nutrient value;
the computer system determining a dietary goal nutrient value;
the computer system comparing the dietary goal nutrient value to the consumed nutrient value to identify a nutrient and a target nutrient value of a nutrient to be consumed to meet the dietary goal nutrient value of an identified nutrient;
the computer system accepting input to select at least one identified nutrient to be consumed to meet the dietary goal;
the computer system recommending a next meal wherein the next meal has at least one selected nutrient identified in the target nutrient value;
the computer system calculating a cost per nutrient of the selected nutrient associated with the next meal;
the computer system calculating the cost of purchasing the next meal;
the computer system conveying the cost of purchasing the next meal to the user; and
the computer system displaying the next meal that provides the target nutrient amount identified by the user and the cost per selected nutrient of the next meal.

2. The method of claim 1 further comprising:
the computer system recommending a next meal wherein the nutrient value of the selected nutrient of the next meal is approximately equal to the target nutrient value of the selected nutrient.

3. The method of claim 2 wherein the step of recommending a next meal further comprises:
the computer system storing at least one menu item within a storage device, the menu item associated with a nutrient value;
the computer system identifying a next meal recommendation by comparing the target nutrient value to the nutrient value of the menu item, the next meal recommendation identified as the at least one menu item that meets the criteria for the target nutrient value; and
the computer system displaying the next meal recommendation.

4. The method of claim 3 further comprising:
the computer system associating each menu item with a location identifier that identifies the location of the menu item.

5. The method of claim 4 wherein the location identifier notifies the user of the menu items that were previously stored by the user.

6. The method of claim 5 further comprising:
a cost identifier that reflects the price at which the user may obtain the menu item; and
the location identifier indicates a location where the user may obtain the menu item.

7. The method of claim 6 further comprising:
the computer system determining the location of the user and the location of the menu item;
the computer system calculating the travel expenses and the time to obtain the menu item;

the computer system calculating the cost identifier by adding the price of the menu item, the travel expenses, and the elapsed time to obtain the menu item to calculate the total costs of obtaining the menu item; and the computer system identifying the next meal recommendation and the cost identifier of the next meal recommendation.

8. The method of claim 3, the step of recommending a next meal further comprises:

the computer system accepting user input to identify a health status of the user;

the computer system considering the health status of the user to recommend the next meal wherein the health status is considered when identifying the next meal recommendation.

9. The method of claim 8 wherein the health status is the blood sugar level of the user.

10. The method of claim 9 wherein the health status is selected from the group consisting of metabolic rate, blood pressure, cholesterol level; weight, and triglyceride level.

11. The method of claim 10 wherein said nutritional value comprises a calorie content and at least one of the following: a macronutrient content, a micronutrient content, a USRDA content, an amino acid content, a fatty acid content, a mineral content, a vitamin content, a cholesterol content, an antioxidant content, an element content, a compound content, a preservative content, a gluten content, a wheat content, a whole grain content, an artificial flavoring content, an allergen content, a probiotic content, an age, an approval status with doctor's orders, an approval status with existing medications, a recommendation status for a particular diet, an organic food status, a use by date, an origin of a food, a trans fat content, a sugar content, a fiber content, a personal preference content, or a personal historical entry.

12. The method of claim 7 further comprising:

the computer system associating a menu item with a preparation time; and the computer system displaying the next meal recommendation and the associated preparation time for the next meal recommendation.

13. A device for monitoring a user's diet and providing a user with the cost information for purchasing a food item per a budget, the device implemented on a computing system including a processing device and an input device, the device comprising:

the computing system configured to accept a user input from the user with the input device, the user input related to a food intake by the user;

the computing system configured to identify a nutrient value associated with the food intake;

the computing system configured to sum the nutrient value of the food intake consumed during a determined period of time to calculate a consumed nutrient value;

the computing system configured to determine a dietary goal nutrient value;

the computing system configured to calculated a consumed nutrient value identifying the amount of nutrients consumed by the user;

the computing system configured to compare the consumed nutrient value to a dietary goal nutrient value to identify at least one nutrient to be consumed to meet the dietary goal nutrient value;

the input device configured to accept a user input to select at least one identified nutrient to be consumed;

the computing system configured to identify at least one food item that has at least one selected nutrient;

the computing system configured to calculate the cost of acquiring a selected food item from a store;

the computing system configured to calculate a cost per nutrient associated with the selected food item and the selected nutrient; and the computer system configured to display the cost per nutrient of the selected food item and the selected nutrient.

14. The device of claim 13 further comprising:

a price associated with the selected food item;

a brandname associated with the selected food item;

a size associated with the selected food item;

a store associated with the selected food item wherein the store is associated with a physical address;

a location of the selected food item in said store, nutritional information associated with the selected food item;

a product history associated with the selected food item; and a personal purchase history associated with the selected food item.

15. The device of claim 14 further comprising:

the computing system configured to compare the cost of the selected food item at a first store with the cost of the selected food item at a second store.

16. The device of claim 15 further comprising:

the computing system configured to compare the cost per nutrient of the selected food item at said first store with the cost per nutrient of the selected food item at said second store.

17. The device of claim 16 wherein the cost per nutrient of the selected food item at said store is calculated by dividing the nutrient value of the selected food item by the cost of the item at the store.

18. The device of claim 17 further comprising:

the computing system configured to determine the location of the user and the location of the selected food item;

the computing system configured to calculate the travel expenses and the time to acquire the selected food item; and the computing system configured to calculate the cost of the selected food item by summing the price of the selected food item at the store, the travel expenses to the store, and the time to obtain the selected food item at the store to calculate the cost of the selected food item.

19. A device for monitoring a user's diet and providing a user with the cost information for purchasing a food item per a budget, the device implemented on a computing system including a processing device and an input device, the device comprising:

the computing system configured to accept a user input from the user with the input device, the user input related to a food intake by the user;

the computing system configured to identify a nutrient value associated with the food intake;

the computing system configured to sum the nutrient value of the food intake consumed during a determined period of time to calculate a consumed nutrient value;

the computing system configured to determine a dietary goal nutrient value;

the computing system configured to compare a consumed nutrient value identifying the nutrients consumed by a user during a predetermined time period to a dietary goal nutrient value for the predetermined time period that identities at least one nutrient to be consumed and the quantity of the nutrient to be consumed during the predetermined time period;

the input device configured to accept a user input identifying at least one selected nutrient;

the computing system configured to identify at least one food item comprising the selected nutrient wherein the selected nutrient is found in the dietary goal nutrient value;

the input device configured to accept user input identifying a selected food item;

the computing system configured to calculate the cost of acquiring the selected food item from a store;

the computing system configured to identify the total number of selected nutrients in the food item;

the computing system configured to calculate a cost per selected nutrient associated with the food item; and the computer system configured to display the food item and the cost per desired nutrient of the food item.

20. The device of claim 19 further comprising:

the computing system configured to compare the cost per nutrient of the selected food item at a first store with the cost per nutrient of the selected food item at a second store, the computing system configured to determine the location of the user and the location of the selected food item;

the computing system configured to calculate the travel expenses and the time to acquire the selected food item; and the computing system configured to calculate the cost of the selected food item by summing the price of the selected food item at the store, the travel expenses to the store, and the time to obtain the selected food item at the store to calculate the cost of the selected food item at the store.

* * * * *